United States Patent [19]
Hartley et al.

[11] Patent Number: 5,970,782
[45] Date of Patent: Oct. 26, 1999

US005970782A

[54] GRADIENT FILTRATION APPARATUS

[75] Inventors: James L. Hartley, Frederick, Md.; Terry A. Landers, Moraga, Calif.

[73] Assignee: Life Technologies, Inc., Rockville, Md.

[21] Appl. No.: 09/079,174

[22] Filed: May 15, 1998

Related U.S. Application Data

[60] Provisional application No. 60/046,694, May 16, 1997.

[51] Int. Cl.[6] .............................. G01N 15/08; B07B 1/50
[52] U.S. Cl. ........................................... 73/38; 210/321.75
[58] Field of Search ........................... 73/863.23, 863.24, 73/863.25, 38; 210/321.75, 321.84

[56] References Cited

U.S. PATENT DOCUMENTS

| | | |
|---|---|---|
| 3,075,891 | 1/1963 | Elam ....................................... 202/188 |
| 3,221,878 | 12/1965 | Brett . |
| 3,591,493 | 7/1971 | Zeineh . |
| 3,764,480 | 10/1973 | Jedlicka et al. . |
| 3,817,379 | 6/1974 | Zipilivan et al. .......................... 210/94 |
| 3,929,583 | 12/1975 | Sharpe et al. . |
| 3,963,355 | 6/1976 | Aldridge, Jr. et al. . |
| 3,976,457 | 8/1976 | Martin . |
| 4,162,850 | 7/1979 | Warren . |
| 4,181,501 | 1/1980 | Keese et al. . |
| 4,225,669 | 9/1980 | Melnick et al. . |
| 4,409,820 | 10/1983 | Nash . |
| 4,558,012 | 12/1985 | Nygren et al. . |
| 4,837,145 | 6/1989 | Liotta . |
| 5,674,395 | 10/1997 | Stankowski et al. .............. 210/321.75 |

FOREIGN PATENT DOCUMENTS 2077132   12/1981   United Kingdom .

OTHER PUBLICATIONS

Pelczar, Michael J., Jr., *Laboratory Exercises in Microbiology*, McGraw–Hill Book Co., 2$^{nd}$ Edition, (1965) Preface, Exercise 51, pp. 269–273 and Exercise 53, pp. 281–286.

Skoog, Douglas A. and West, Donald M., *Fundamentals of Analytical Chemistry*, 2$^{nd}$ Edition, (1969) pp. 1–6.

Wistreich, George A. and Lechtman, Max D., *Microbiology* 3$^{rd}$ Edition, Glencoe Publishing Co., Inc., (1980) Preface and pp. 264–265.

Freshney, R. Ian, *Culture of Animal Cells, A Manual of Basic Technique*, Alan R. Liss, Inc., New York, Preface and Chapter 19, Quantitation and Experimental Design (1983) (pp. 199–215).

Horwitz, William, *Official Methods of Analysis of the Association of Official Analytical Chemists*, 13$^{th}$ Edition, Published by: Association of Official Analytical Chemists (1980) pp. 846–849.

McCrane, Walter C., and Dely, John Gustav, *The Particle Atlas*, Edition Two, vol. I Principles and Techniques, Ann Arbor Science Publishers, Inc. (1973) pp. 204–271.

*Primary Examiner*—Hezron Williams
*Assistant Examiner*—Jay L. Politzer
*Attorney, Agent, or Firm*—Sterne, Kessler, Goldstein & Fox P.L.L.C.

[57] ABSTRACT

Particles such as bacteria may be enumerated from a liquid in an accurate and efficient manner through use of an apparatus including a filter sheet which is oriented transverse to the surface of the liquid being filtered. The filter sheet is so arranged so that, as the liquid is filtered, an increasing portion of the filter is above the surface of the liquid. As a result of the surface of the liquid dropping across the filter, a smaller fraction of the total volume of the liquid passes through the upper portion of the filter than through the lower portion of the filter. Since the number of bacteria trapped per unit area of the filter depends on the volume filtered through the area, a monotonically increasing gradient of density of filtered bacteria occurs from the top to the bottom of the filter.

2 Claims, 5 Drawing Sheets

5,970,782

GRADIENT FILTRATION APPARATUS

CROSS REFERENCE TO RELATED APPLICATION

This application claims priority to U.S. Provisional Application No. 60/046,694, filed May 16, 1997, the entire contents of which are considered as being part of the disclosure of the accompanying application and are hereby incorporated by reference therein.

BACKGROUND OF THE INVENTION

This invention relates to devices for collecting particles such as cells suspended in liquids, and solutes carried in solvents. More particularly, the invention relates to filter devices for distributing particles or solutes in a graduated fashion to allow enumeration over a wide range of particle or solute concentrations.

Enumeration of microorganisms in water, foods, pharmaceuticals, etc., is commonly done by the application of samples to petri plates containing mixtures of nutrients and agar. Individual cells multiply on the surface of the agar to form visible colonies which are then counted. Since the number of organisms in the sample is unknown, a series of dilutions is usually prepared and aliquots (usually 0.1 mL) of each dilution are spread on the agar surface. The number of colonies per standard (10 cm) plate should be above 30 (for statistical significance) and below 300 (above which point overlapping colonies become more likely), unless more elaborate methods are used (Arthur L. Koch in *Manual of Methods for General Bacteriology*, Philipp Gerhardt, ed., American Society for Microbiology, 1981, p. 185).

An alternative known method for determining bacterial counts is to pass the sample through a membrane filter which retains the bacteria on its surface. The filter is then placed on the surface of an agar plate. Nutrients diffuse through the membrane allowing cells to grow into visible colonies. Advantages of membrane filtration are that (i) large volumes can be filtered to enumerate bacteria in dilute samples; and (ii) distribution of cells over the filter is uniform, a result that is difficult to achieve with spreading methods. Accurate quantitation, however, often requires multiple dilutions and filtrations, which are laborious and expensive.

SUMMARY OF THE INVENTION

It is an object of the invention to enumerate particles such as bacteria from a liquid in an accurate and efficient manner.

Another object is to provide an improved apparatus for quickly and precisely enumerating bacteria in a liquid.

A further object is to provide an improved particle filtering apparatus which is inexpensive to construct yet easy to use and effective in operation.

Other objects will be apparent from the description to follow and from the appended claims.

The invention provides the advantages of making a series of dilutions for successive filtrations, without actually having to do so. It accomplishes this result by passing widely varying volumes of sample through different portions of a single filter, all in the same operation. The same inventive concept can be used to make a filter having regions with differing pore sizes. In this embodiment, different volumes of an agent which etches or dissolves the filter are passed through different regions of the filter, resulting in different times of exposure to the etching agent.

The invention in its preferred form includes a filter sheet which is transverse to the surface of the liquid being filtered and arranged so that as the liquid is filtered, an increasing portion of the filter is above the surface of the liquid. As a result of the surface of the liquid dropping across the filter, a smaller fraction of the total volume of the liquid passes through the upper portion of the filter than through the lower portion of the filter. Since the number of bacteria trapped per unit area of the filter depends on the volume filtered through that area, in this construction a monotonically increasing gradient of density of filtered bacteria occurs from top to bottom of the filter.

DESCRIPTION OF THE PREFERRED EMBODIMENT

Figure 1:
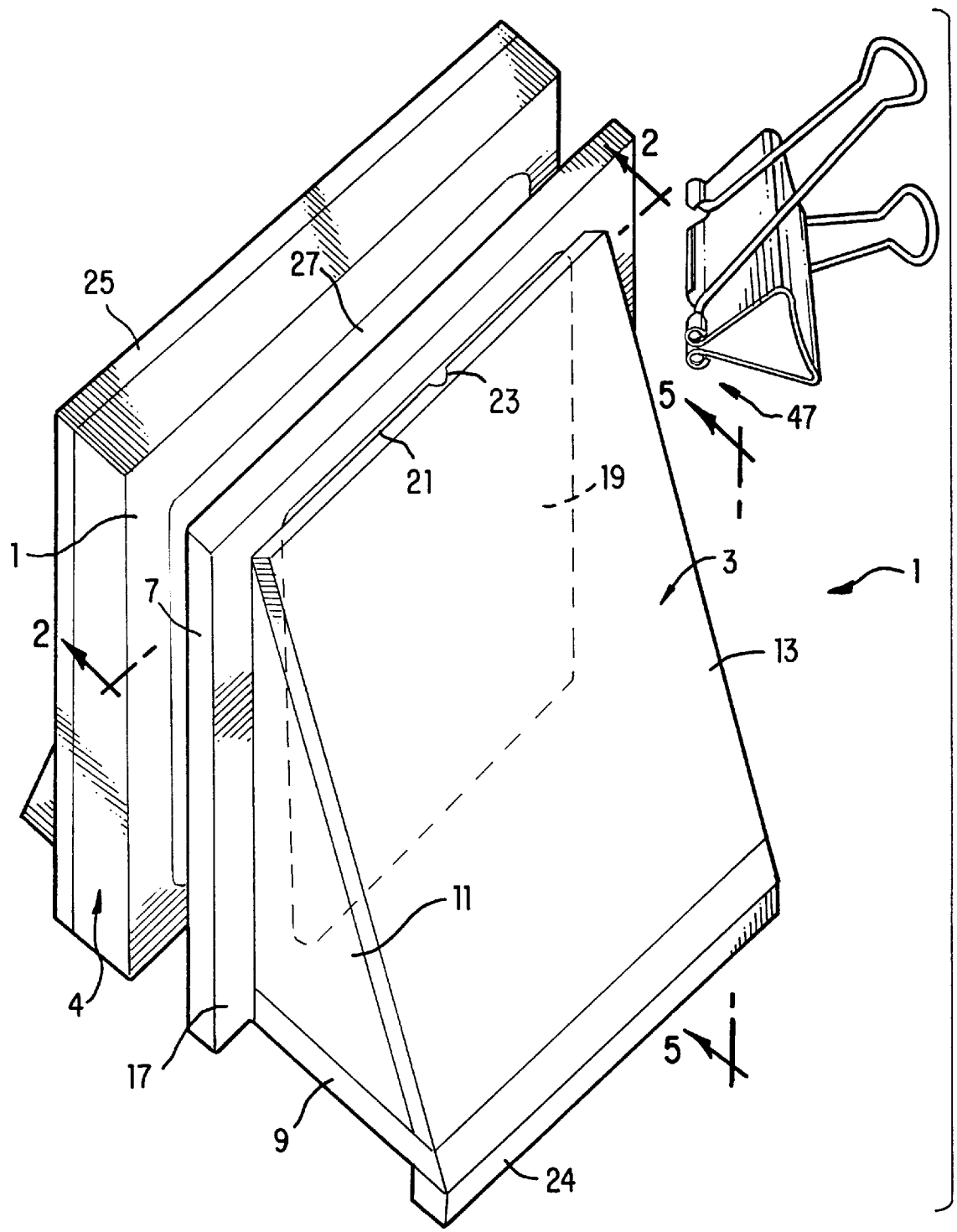
FIG. 1 is an exploded perspective view of the preferred embodiment of a filter apparatus according to the invention.

Referring to FIGS. 1–5, a filter apparatus 1 according to the invention is shown. The apparatus includes a forwardly disposed sample chamber assembly 3 and a rearwardly disposed filter support assembly 4. Assembly 3 is composed of a frame 7, a base 9, side walls 11 and a rearwardly inclined front wall 13. Frame 7, base 9, and walls 11, 13 define the forward portion of a sample chamber 15. Frame 7 includes a border section 17 defining a central opening 19. The upper edge of wall 13 terminates below the upper border portion of frame 7 to define a ventilation gap 21 to chamber 15. A fill port 23 is provided at the top of wall 13 for pouring liquid into chamber 15. A support leg 24 is attached to the forwardmost portion of the underside of base 9 to stabilize the apparatus during filling with liquid.

Figure 2:
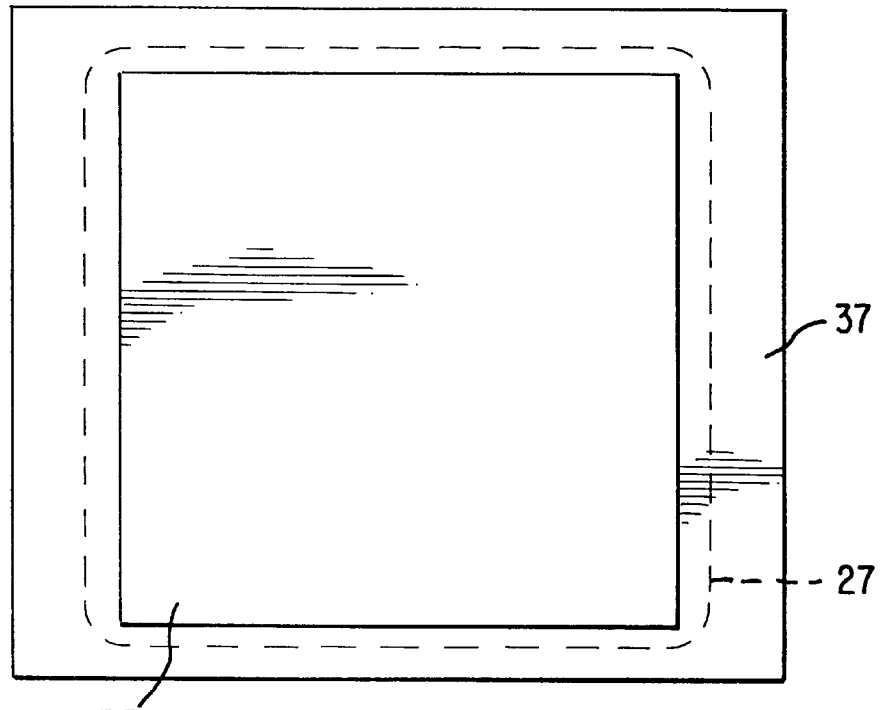
FIG. 2 is a view taken in the direction 2—2 as shown in FIG. 1.
Figure 3:
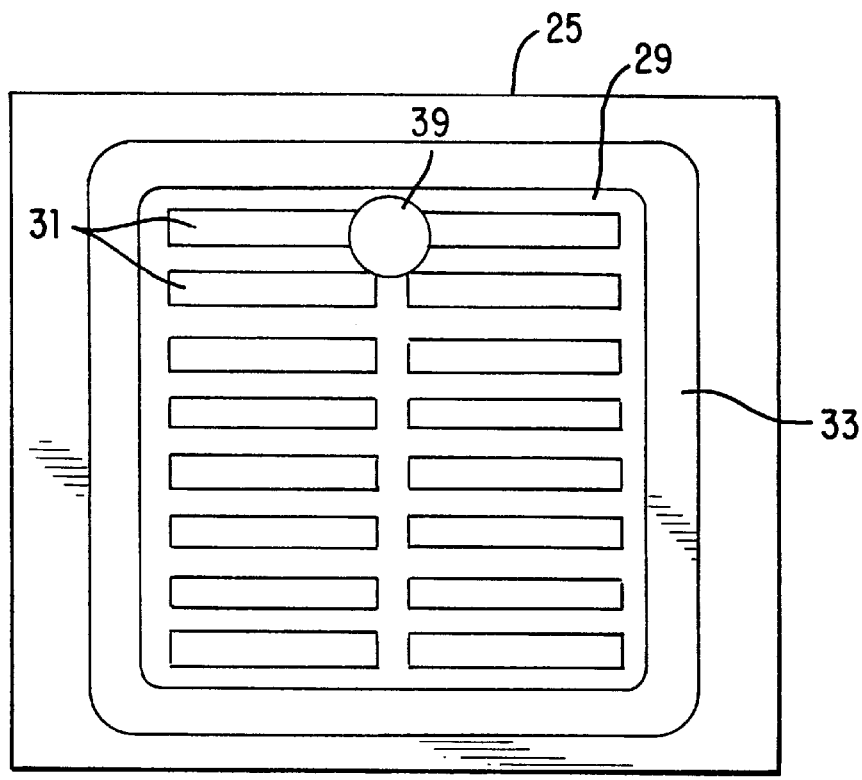
FIG. 3 is a front view of the apparatus shown in FIG. 2, but with the forwardly disposed porous sheet and adhesive tape removed.
Figure 4:
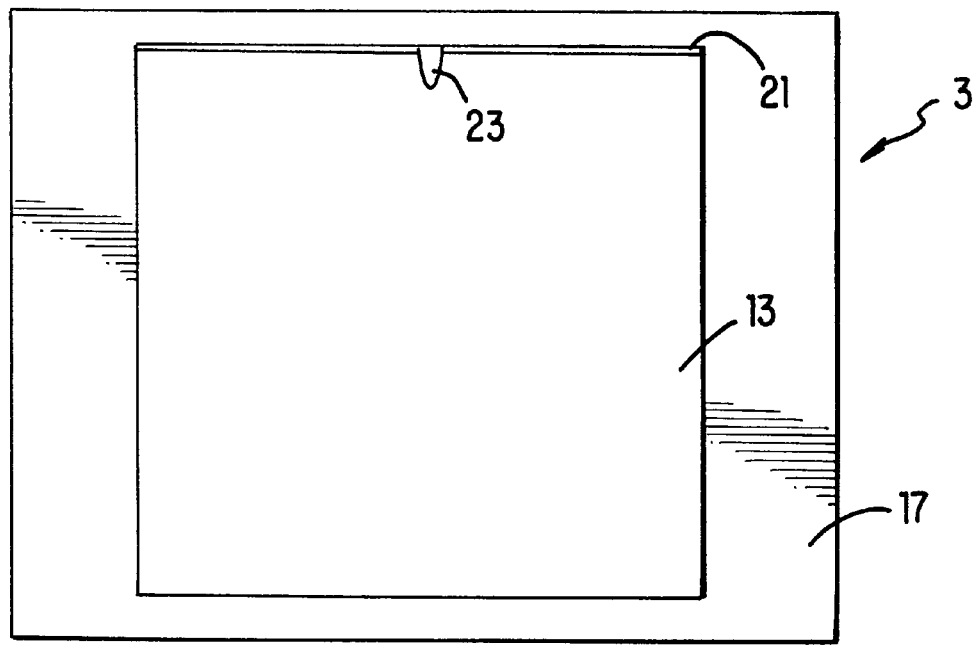
FIG. 4 is a front view of the apparatus of FIG. 1.
Figure 5:
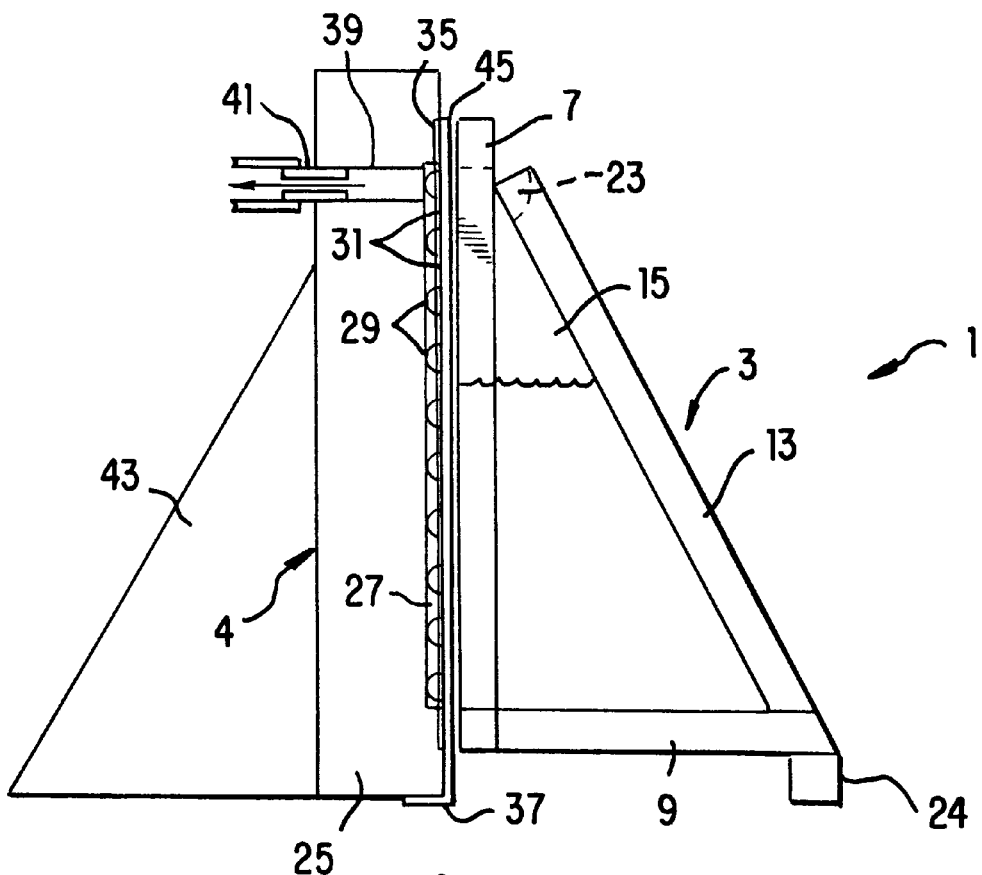
FIG. 5 is a sectional view taken in the direction 5—5 of FIG. 1.

Filter support assembly 4 includes a support block 25 in which is located a central recess 27 which is opposite and slightly larger than opening 19 in frame 7. Referring to FIG. 3, a pattern of channels 29 is defined by a series of ridges 31 and a peripheral lip 33 whose height above the base of channels 29 is the same as the height of ridges 31. The co-planar forward surfaces of ridges 31 and lip 33 are below the forward surface of support block 25. A porous support sheet 35, shown in FIG. 2, is secured on the forward surfaces of ridges 31 and lip 33 by adhesive tape 37. Sheet 35 has a size commensurate with the central recess 27. The depth of lip 33 is slightly less than the thickness of sheet 35 so that the sheet can be securely compressed when apparatus 1 is assembled. A port 39 extends through block 25 for evacuating fluid from recess 27. Port 39 is preferably at the upper edge of central recess 27 to minimize filtration due to gravity flow during the filling of chamber 15 although a hose clamp could be used to prevent flow prior to the application of suction as discussed below. A hose nipple 41 can be fit into port 39 for connection to a vacuum source. A pair of support braces 43 (FIG. 5) are attached to the rear face of block 25 for stabilizing apparatus 1 to maintain the filter sheet discussed above at its desired orientation.

A filter sheet 45 must be secured across the exposed portion of porous support sheet 35. This is accomplished by clamping the sample chamber assembly 3 to filter support assembly 4 so that border section 17 of frame 7 compresses the edge portions of filter sheet 45 against tape 37 holding porous support sheet 35 in place. This can be accomplished by clamping means such as binder clips 47, one of which is shown in FIG. 1, the one on the opposite side of apparatus 1 having been omitted for clarity. (The clips have also been omitted from FIG. 4). It is important that a fluid seal exists around the edge portion of filter sheet 45 to confine fluid flow through a defined area of the filter sheet and into recess 27.

Filter sheet 45 is preferably a membrane filter which does not permit air flow when wetted, and a nitrocellulose membrane is a suitable material. We prefer filters with a pore size of ½ micron or less for most applications; other standard membrane filters will be chosen as suitable for a particular use according to considerations known to those skilled in the art. Porous sheet 35 should be an inert material having a compressible border portion which minimizes distortion of the membrane filter during filtration; porous polyethylene sheeting is appropriate for this purpose.

The various wall structures comprising apparatus 1 should be impervious to gas and liquid. Thus, front wall 13, frame 7, base 9, block 25 and braces 43 are preferably constructed of Plexiglas (methylmethacrylate), molded polystyrene, or polycarbonate.

Because the filter is not horizontally mounted, as noted above, more liquid is filtered through a lower region of the filter than through an upper region of the same area. But an important further advantage of the invention is that this effect may be greatly enhanced by providing a liquid sample chamber which narrows toward the top. In the preferred embodiment, for example, the chamber wall opposite the filter is rearwardly inclined-that is, it is inclined toward the filter at the top to form a chamber substantially triangular in cross-section.

Figure 6:
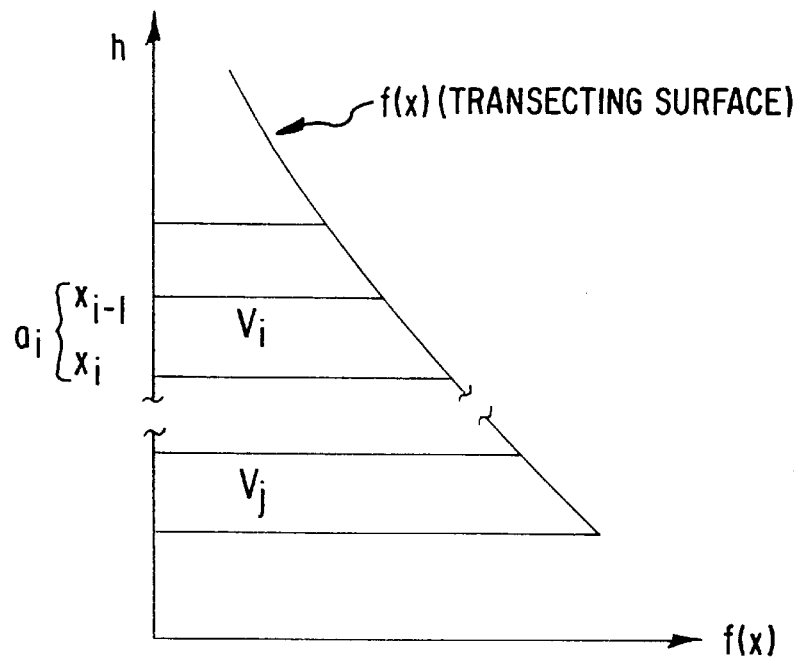
FIG. 6 is a graphical representation of the equation describing the cross section of filtration chamber which can be incorporated in the apparatus of FIG. 1.

The configuration of the chamber and the orientation of the filter determine the distribution of analyte across the filter. A mathematical description of the distribution of analyte as a function of sample chamber shape follows. In the case of a sample chamber such as chamber 15 which is essentially a cube with the filter-forming one vertical wall and a surface such as the rearwardly facing surface of front wall 13 transecting the cube and forming the opposite wall, the volume filtered through a given filter area can be calculated as follows, with reference to the curve shown in FIG. 6 (wherein the curve represents the foregoing opposite wall in general terms such that at a height, x, the horizontal distance from the filter to the foregoing opposite wall is f(x)):

The total height, h, of the chamber is divided into n equal intervals by lines at heights h=$x_o$, $x_1$, ..., $x_i$, ..., $x_n$, to give areas $a_1$, ..., $a_i$, ..., $a_n$ where $$a_1 = a_2 \ldots = a_i = \ldots = a_n = w(x_i - x_{i-1}) = hw/n \qquad \text{(eq 1)}$$

and w is the width across the face of the filter. The volume, $v_i$, opposite an area $a_i$ (bounded by heights $x_i$ and $x_{i-1}$) is given exactly by $$v_i = w \int_{x_{i-1}}^{x_i} f(x) dx \qquad \text{(eq 2)}$$

where f(x) is the function describing the horizontal distance from the filter to the transecting surface as noted above. For purposes of calculation, the volume is given approximately by the trapezoidal rule for numerical integration by $$v_i = [wh/(2n)][f(x_i) + f(x_{i-1})]. \qquad \text{(eq 3)}$$

During filtration $v_i$ is distributed uniformly across the remaining submerged n–i areas and thus contributes $v_i/(n-i)$ to the total volume filtered through an area $a_j$ (j i) below it. Therefore the total volume $V_j$ filtered through each area $a_j$ is approximately $$v_j = ([wh/(2n)])\sum_{i=1}^{j} [f(x_i) + f(x_{i-1})][1/(n-i)] \qquad \text{(eq 4)}$$

(Note: the exact description of $V_j$ gives an integral of the type $$\frac{f(x)}{(a+bx)} dx.$$

For the tables and experiments described below, required numerical values were determined by equation 4 using numbers on the order of 10,000 for n. One should also note that an empirical description of the distribution of analyte could be made by filtering several samples of known particle concentration through such a device and then determining the number of particles in the areas, $a_1$.

Figure 7A:
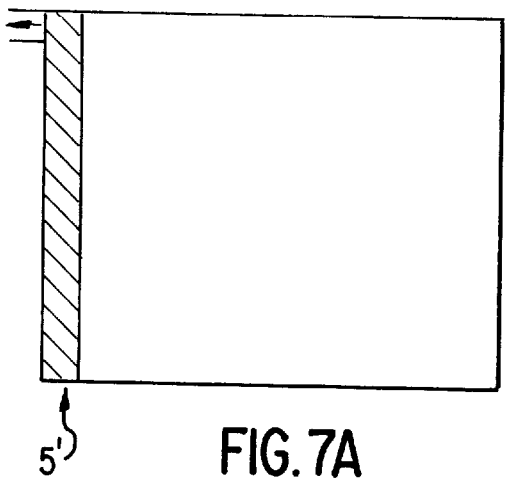
FIG. 7 shows the cross sections of sample chambers of various geometries which could be used in the apparatus of FIG. 1.
Figure 7C:
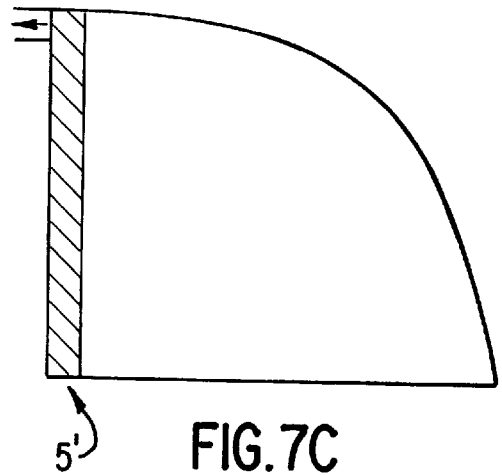
Figure 7B:
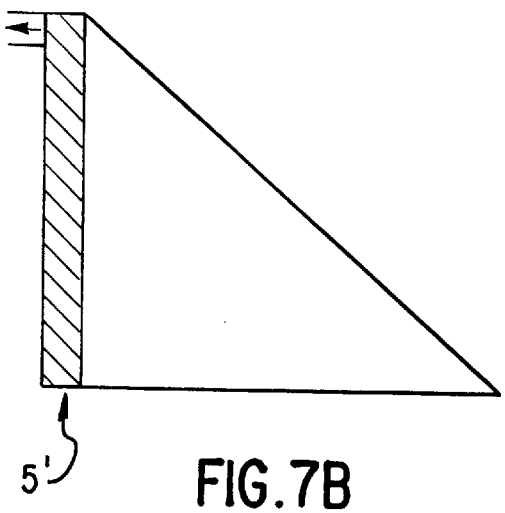
Figure 7D:
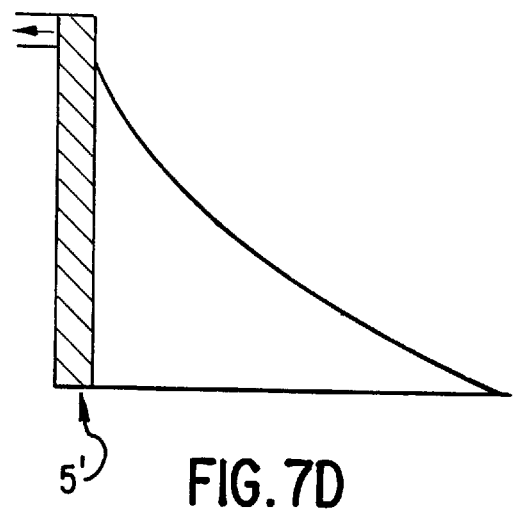

These equations have been applied to sample chambers of various shapes. Referring to FIG. 7, various versions of apparatus 1 are shown including filter support assemblies 5' and sample chamber assemblies having vertical filters and walls opposite those filters which are respectively vertical (FIG. 7A) to form a rectangular chamber, inclined (FIG. 7B) to form a triangular chamber, logarithmic (FIG. 7C), and parabolic (FIG. 7D). If the transecting surface is a plane which forms a chamber rectangular in cross section (FIG. 7A), approximately 64 times as much of the liquid is filtered through the bottom tenth as through the top tenth of the filter. If the chamber is triangular in cross section (FIG. 7B), approximately 1344 times as much of the liquid is filtered through the bottom tenth as through the top tenth of the filter. More complex geometries can be found to give other proportions. Examples of these are shown in the following Table 1:

TABLE 1

| Shape (FIG. 7) | Relative volume filtered top 1/10: bottom 1/10 |
| --- | --- |
| Rectanqular (FIG. 7A) | 1:64 |
| Triangular (FIG. 7B) | 1:1344 |
| Logarithmic (FIG. 7C) | 1:830 |
| Parabolic (FIG. 7D) | 1:19000 |

As noted above, a triangular chamber filters 1344 times as much volume through the bottom tenth as through the top tenth of the filter. The same chamber filters 7548 times as much volume through the bottom twentieth as through the top twentieth. Thus if it is possible to examine smaller portions of the filter (twentieths, hundredths, etc.), the useful range of any shaped chamber can be greatly increased. One way to do this is to increase the absolute size of the device.

It may be desired for some applications to be able to specify a particular relationship between the number of particles or quantity of material deposited on or flowing though adjacent segments of a filter. This could be accomplished in two ways:

(1) Given a desired distribution of $V_i^1$ s, $V_1$, $V_2$, . . . Vn to be filtered through area $a_1$, $a_2$, . . . $a_n$, one need only solve Equation 4 for each $f(x_i)$ in turn, beginning with i=1, to approximate the curve of the chamber wall which will yield that desired distribution:

$$f(x_j) = \frac{2n(n-j)(V_j - V_{j-1})}{wh} - f(x_{j-1}).$$

(2) Using Equation 4, a set of graduated areas could be determined such that successive segments contain the desired fraction of analyte, e.g., 1/1024, 1/512, 1/256, etc. This would yield a table of dilution multipliers like Table 2 in which the multiplier values are regular multiples of some chosen number, more familiar to those accustomed to standard dilution techniques.

The device employs a membrane filter, allowing samples too dilute for direct spreading on agar plates to be filtered and counted. However, in contrast to conventional membrane filtration devices, it will also allow enumeration from relatively concentrated samples. In conventional membrane filtration, such samples must be diluted and each dilution individually filtered to ensure that a statistically meaningful number of colonies appears on one of the filters. The device described here eliminates or greatly reduces the need for multiple dilutions and filtrations because the geometrically defined "gradient manner" of deposition of bacteria (or other analyte) on the filter deposits a very small fraction of the sample in the first (top) tenth or twentieth of the filter. This allows accurate enumeration over a much wider range of concentrations.

As shown in the example described below, this device gives reliable quantitation for bacteria at concentrations ranging from 25 to at least 25,000 cells per sample without requiring any dilutions.

A device was constructed of Plexiglas and porous polyethylene as shown in FIG. 1. The right trapezoidal chamber 15 was dimensioned to have a capacity of approximately 140 mL. The filtration area of the device was approximately 7.7 cm×7.7 cm. The filter material was nitrocellulose membrane, having a 0.45 micron pore size and sides measuring 9 cm×9 cm.

A suspension of *Escherichia coli* was prepared from a colony on a plate and diluted in a series of four-fold steps from 1/1 to 1/1024 in saline, giving a final volume of 7.5 mL for each dilution. Four aliquots of 0.1 mL of the 1/16, 1/64, and 1/256 dilutions were spread on agar plates for "plate counts."

The average number of colonies counted on quadruplicate plates was 10.5 at a dilution of 1/256, 43.7 at 1/64 and 185.5 at 1/16. Since 0.1 mL aliquots were plated, the initial dilution (1/1) must have contained about 28,200 cells per mL.

Four filtration samples were prepared from each of the dilutions above by adding 1 mL of the dilution to 140 mL of saline containing 50 ng/mL of basic fuchsin. Each filtration sample was poured into the assembled filtration device and vacuum was applied until all liquid had been removed from the chamber. The filters, which exhibited a graduated pink stain due to the basic fuchsin, were placed on agar plates overnight to allow the bacterial cells to grow into colonies. Afterward the filters were dried briefly and immersed in a blue staining solution ("Bradford reagent," BioRad Laboratories) for about one minute which stained the exposed nitrocellulose blue. The filters were transferred to water and the bacterial colonies scraped off, revealing white spots that had not been stained.

Figure 8:
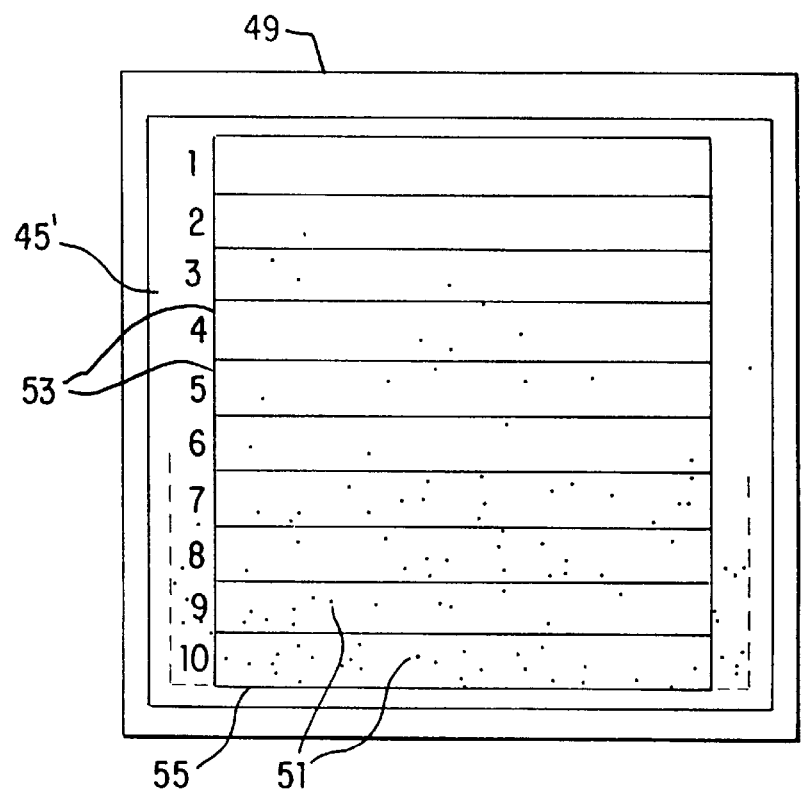
FIG. 8 is a front view of a membrane filter after performance of a filtering operation, with a transparent counting overlay.

Referring next to FIG. 8, a transparent counting overlay 49 is shown positioned over a filter sheet 45' on which appear white spots 51 where bacterial colonies have prevented filter sheet 45' from being stained blue. Counting overlay 49 is marked off with ten equal size segments 53, numbered 1–10. Each segment 53, for the example shown, is approximately 6.6 cm. wide and 0.75 cm. high. The counting overlay is aligned at the bottom of the filter by positioning the lowest line of the counting overlay over the lower edge of pink basic fuchsin stain, which indicates the lower margin of the filtration area as identified by the numeral 55 in FIG. 8. In a manufactured device, it may be desired to have the lines defining the segments printed directly on the filter to eliminate the need for a counting template.

A table of "dilution multipliers," $D_j$, was calculated for this combination of device and template as follows: the dimensions of the device chamber were used to calculate, by numerical integration using equation 4, the fraction of the total volume filtered through each successive tenth of a filter ($V_j$'s). The running sum of these values was multiplied by the fraction of the filtration area contained in the template ($a_T$, 0.835 in this example), then divided into one, to obtain the multiplier found in the following Table 2 using the formula $D_j = 1/(a_T V_j)$:

TABLE 2

| Number of Segments Counted | Dilution Multiplier |
| --- | --- |
| 1 | 704 |
| 2 | 147 |
| 3 | 55 |
| 4 | 26 |
| 5 | 14 |
| 6 | 8.4 |
| 7 | 5.2 |
| 8 | 3.3 |
| 9 | 2.1 |
| 10 | 1.2 |

Colonies on each filter were counted, using the counting template, starting with the top tenth and continuing down the filter. Segments containing more than 300 to 350 colonies could not be counted accurately and were not used for calculations. The sum of the colonies counted on each filter was tabulated. The average sums for sets of four filters at each dilution are shown in table 3, with the number of segments counted from the top down to arrive at that sum.

TABLE 3

| Dilution | Segments Counted | Colonies Counted | Dilution Multiplier | Calculated Col/mL | Actual Col/mL* |
| --- | --- | --- | --- | --- | --- |
| 1/1 | 3 | 485 | 55 | 26,700 | 28,200 |
| 1/4 | 5 | 486 | 14 | 6,800 | 7,050 |
| 1/16 | 8 | 565 | 3.3 | 1,860 | 1,760 |
| 1/64 | 10 | 356 | 1.2 | 427 | 440 |

TABLE 3-continued

| Dilution | Segments Counted | Colonies Counted | Dilution Multiplier | Calculated Col/mL | Actual Col/mL* |
|---|---|---|---|---|---|
| 1/256 | 10 | 94 | 1.2 | 113 | 110 |
| 1/1024 | 10 | 21 | 1.2 | 25 | 28 |

*Based on average plate count for dilutions 1/16, 1/64, and 1/256.

The table shows the average number (for four filters) of colonies counted, the number of segments (from the top) containing those colonies, the appropriate dilution multiplier (from Table 2), the calculated cells per mL for that dilution (obtained by multiplying the number of colonies counted by the dilution multiplier), and the approximate number of colonies per mL in that dilution as calculated from the plate count. Using the filtration device, single filtrations gave accurate quantitation of bacterial cells when compared to plate count results. This was true even when one mL containing more than 20,000 cells per mL was filtered. At this concentration a direct plate count or conventional membrane filtration would have yielded colonies many times too numerous to count without further dilutions. The utility of the device for the generation of reproducible and mathematically predictable gradients of bacteria (or other analyte) on a filter, with concomitant avoidance of multiple dilutions, is thus demonstrated.

The example of the preferred embodiment of the invention related to the counting of bacteria on a filter which was removed from the device for culture and enumeration. It is also possible to culture and enumerate the bacteria on the filter without complete disassembly of the device. If the filter is securely fixed to the sample assembly chamber 3, e.g. by glue or a "sonic weld," the chamber with filter attached can be removed from the filter support assembly and placed, filter side down, on a nutrient-containing pad or agar plate for culture. If the filter sheet 45 was previously imprinted with segment-defining lines and the rearwardly inclined front wall 13 is transparent, the number and location of colonies can be visually or optically determined without exposing the observer directly to the organism. This would be of great value in handling particularly pathogenic or virulent organisms. One might also adapt the principles of U.S. Pat. Nos. 3,817,379 (Zipilvan, et al.) and 3,741,877 (Shaufus, et al.) to effect the removal of liquid from the chamber and culture of the organism without need for use of a vacuum source or any disassembly of the device.

In this alternative embodiment of our invention, cultures of anaerobic organisms may be grown as well. It is only necessary to coat the exterior surface of the filter, after the organisms are deposited thereon, with a suitable compound which will make it airtight without being toxic to the organism, or provide a covering structure and seal it to the sample assembly chamber 3. The chamber is then perfused with any oxygen-free gas, such as $N_2$, suitable for the organism to be cultured, and the fill port 23 is closed by a sonic weld, adhesive compound, or other means, to render the chamber airtight. With a transparent front wall 13, the growth of the culture can be followed with time. This presents a great advantage over previous methods, in which serial cultures have to be grown because examining a culture necessitates its exposure to the air.

The invention can be used to count other particles and solutes as well. Other types of detection would be appropriate for other types of samples. Such methods might include electronic detection, (e.g. visualization by a television camera, or measurement of the change in conductivity or capacitance of the filter); visual, optical or electronic detection of fluorescence or luminescence; gravimetric; microscopic examination and other methods well known to those skilled in the art. Thus, one could use the invention to evaluate the particulate content of solvents intended for use in integrated circuit manufacture by filtering a sample through the device and then examining the surface of the filter microscopically for trapped particles. Rates of wear in lubricated parts of aircraft engines could be measured by determining particle content of lubricants and hydraulic fluids. Solutes which bind to, absorb to or react with the filter material can also be quantitated. An example of such absorption is the graduated pink color seen on the filters described above when basic fuchsin, a soluble dye, is filtered. Had it been desirable, the amount of dye bound to the filter could have been determined spectrophotometrically for each segment. Such a mathematically defined gradient could be of use as a standard for calibration or comparison in other instruments or tests.

In addition to enumeration and quantitation, the apparatus could be used to make graduated modifications to filters for other uses. For example, by filtering a solution capable of enlarging the pores of a filter, for instance by etching neutron activated pores in polycarbonate films (Nucleopore filters), a single filter with graduated pore sizes is produced because the time period of exposure to the etching solution varies from the top to the bottom of the filter. Transferred to the appropriate filtration device, it would provide a simple and rapid way to estimate the size of particles, bacteria or viruses without the cumbersome prior procedure of using a series of filters of graduated pore sizes.

It should be understood that other and equivalent means might be used for passing differing volumes through differing regions of the same filter. For example, a horizontally mounted filter could be covered or backed by a sliding shield which successively exposed an increasing number of regions of the filter, as necessary to produce a desired distribution of volumes through those regions. The specific embodiment discussed herein is preferred because of its convenience of manufacture and use.

The invention has been described in detail with particular reference to the preferred embodiment, but it should be understood that variations and modifications within the spirit and scope of the invention may occur to those skilled in the art to which the invention pertains.

What is claimed is:

1. An improved apparatus for enumerating particles contained in a liquid, said apparatus comprising a chamber for containing said liquid and having an opening in a side thereof;

a filter-carrying member; a generally flat filter for retaining said particles when said liquid is passed through said filter, said filter-carrying member supporting said filter in said opening to cause liquid flowing from said chamber to pass through said filter, said filter being disposed in the apparatus such that the level of the liquid passing from said chamber through said filter falls from an upper portion of said filter down to a lower portion of said filter, causing a lesser volume of said liquid per unit area to pass through said upper portion than through said lower portion and means for determining the numbers of said particles retained by said upper and lower portions of said filter.

2. The improved apparatus of claim 1 and in which said chamber is of lesser volume at the top than at the bottom thereof, and the surface area of said liquid level decreases by a known or calculable amount as the said liquid level falls.

\* \* \* \* \*